US009636241B2

(12) United States Patent
Su

(10) Patent No.: US 9,636,241 B2
(45) Date of Patent: May 2, 2017

(54) COIL BIOABSORBABLE STENTS

(75) Inventor: Shih-Horng Su, Irvine, CA (US)

(73) Assignee: MANLI INTERNATIONAL LTD (VG)

( * ) Notice: Subject to any disclaimer, the term of this patent is extended or adjusted under 35 U.S.C. 154(b) by 355 days.

(21) Appl. No.: 13/587,219

(22) Filed: Aug. 16, 2012

(65) Prior Publication Data

US 2013/0261733 A1    Oct. 3, 2013

Related U.S. Application Data

(63) Continuation-in-part of application No. 13/435,487, filed on Mar. 30, 2012, now Pat. No. 8,834,915, and
(Continued)

(51) Int. Cl.
*A61F 2/82* (2013.01)
*A61F 2/88* (2006.01)
(Continued)

(52) U.S. Cl.
CPC ................ *A61F 2/88* (2013.01); *A61F 2/885* (2013.01); *A61F 2/954* (2013.01); *A61F 2002/061* (2013.01); *A61F 2002/825* (2013.01); *A61F 2210/0004* (2013.01); *A61F 2230/0067* (2013.01); *A61F 2230/0091* (2013.01); *A61F 2250/0029* (2013.01);
(Continued)

(58) Field of Classification Search
CPC .. A61F 2002/30121; A61F 2002/30123; A61F 2/88; A61F 2/885; A61F 2230/0091
USPC ....................... 623/1.22, 1.27, 1.3, 1.31, 1.17
See application file for complete search history.

(56) References Cited

U.S. PATENT DOCUMENTS 5,133,732 A * 7/1992 Wiktor ...................... A61F 2/88
                                                              604/104
5,582,619 A * 12/1996 Ken .............................. 606/191
(Continued)

FOREIGN PATENT DOCUMENTS

WO     2008-051579     5/2008

OTHER PUBLICATIONS

European Patent Office, Extended Search Report, EP Appln. No. 12195835, Feb. 13, 2013, 1 page.

*Primary Examiner* — Christian Sevilla
*Assistant Examiner* — Cheryl Miller
(74) *Attorney, Agent, or Firm* — Fish & Tsang, LLP

(57) ABSTRACT

An expandable, bioabsorbable stent having a coiled-coil configuration is described. The stent further comprises regions of variable pitch that allow for variation in either rigidity, or variability diameter within sub-regions along the length of the deployed stent. By varying the diameter allows the stent to extend into regions such as branched vessels, or into the neck of aneurysms. In some embodiments, the stent comprises longitudinal support fibers that run substantially the length of the deployed stent to provide additional strength. In addition, the stent may also comprise regional support fibers that run less than the length of the stent, and which provide increased regional strength while permitting flexibility of the stent. The stent further comprises micro-tubes that are configured to be visible using medical imaging techniques. The stent can be manufactured from materials that are bioabsorbable and/or include the ability to release pharmacologically active substances over time.

15 Claims, 3 Drawing Sheets

Related U.S. Application Data a continuation-in-part of application No. 13/476,336, filed on May 21, 2012, now Pat. No. 9,173,752.

(51) Int. Cl.
  *A61F 2/954* (2013.01)
  *A61F 2/06* (2013.01)

(52) U.S. Cl.
  CPC ............... *A61F 2250/0039* (2013.01); *A61F 2250/0067* (2013.01); *A61F 2250/0098* (2013.01)

(56) References Cited

U.S. PATENT DOCUMENTS

| | | | | |
|---|---|---|---|---|
| 5,607,445 A * | 3/1997 | Summers | | 623/1.22 |
| 5,639,277 A * | 6/1997 | Mariant et al. | | 606/191 |
| 5,782,907 A * | 7/1998 | Frantzen | | A61F 2/88 606/108 |
| 5,843,168 A * | 12/1998 | Dang | | A61F 2/88 606/194 |
| 6,162,244 A * | 12/2000 | Braun | | A61F 2/82 623/1.12 |
| 6,497,724 B1 * | 12/2002 | Stevens | | A61F 2/07 623/1.15 |
| 7,128,755 B2 * | 10/2006 | Su et al. | | 623/1.15 |
| 7,412,993 B2 * | 8/2008 | Tzeng | | 140/149 |
| 2001/0020182 A1 * | 9/2001 | Klumb et al. | | 623/1.13 |
| 2002/0029077 A1 * | 3/2002 | Leopold | | A61F 2/07 623/1.11 |
| 2002/0040236 A1 * | 4/2002 | Lau | | A61F 2/07 623/1.12 |
| 2002/0138131 A1 * | 9/2002 | Solovay | | A61F 2/91 623/1.15 |
| 2002/0183830 A1 | 12/2002 | Su et al. | | |
| 2003/0195609 A1 * | 10/2003 | Berenstein | | A61F 2/856 623/1.15 |
| 2005/0080481 A1 * | 4/2005 | Madda | | A61F 2/856 623/1.22 |
| 2005/0085893 A1 * | 4/2005 | Roy | | A61F 2/92 623/1.13 |
| 2005/0203610 A1 | 9/2005 | Tzeng | | |
| 2008/0103584 A1 * | 5/2008 | Su | | A61F 2/91 623/1.16 |
| 2010/0030319 A1 * | 2/2010 | Weber | | A61F 2/88 623/1.11 |
| 2011/0118822 A1 | 5/2011 | Welch | | |

* cited by examiner

COIL BIOABSORBABLE STENTS

PRIORITY CLAIM

This application claims the benefit of priority to and is a continuation-in-part of U.S. patent application Ser. No. 13/435,487, filed Mar. 30, 2012 and U.S. patent application Ser. No. 13/476,336, filed May 21, 2012, both of which are incorporated by reference in their entireties.

FIELD OF THE INVENTION

The field of the invention is related to stents for placement in blood vessels, glands, ducts or organs, and in particular stents that are designed to provide local delivery of therapeutic agents, are bioabsorbable and which can treat occluded or weakened lesions.

BACKGROUND

Stents are commonly used as a means of supporting weakened sections of blood vessels, glands or ducts, to re-open lumens of collapsed or occluded vessels, glands or ducts, or as means for treating aneurysms and other diseases. Stents have also been useful as a means of delivering therapeutic agents to specific sites within the vascular or ductal structures of organs. Stents may also be manufactured to be bioabsorbable such that the body absorbs them over a period of time. However, each of the features creates challenges in the design and manufacture of stents For example, drug-containing stents are constructed of polymeric fibers compounded with the drug of interest. The mixture is then formed into structural elements of a stent by processes such as co-compression molding, co-injection molding, or co-extrusion. For example, in a conventional co-extrusion process, one or more therapeutic agents are compounded with a polymer resin. The compounded resin is then melt extruded to form elongated fibers from which the stent can be fabricated. However, these processes suffer from significant limitations. First, the temperature at which the polymer can be melted may cause degradation of the therapeutic agent.

Similarly, the ratio of drug to polymer may have a significant impact on the strength and/or flexibility of the stent. To overcome this, it is common to maintain the drug-polymer ratio low in order to avoid compromising strength. However, this limits the amount of bioavailable drug that can be packaged within the stent, and which would be available in vivo for therapeutic use.

Other ways in which to provide sufficient structural strength to a stent can involve the use of high or ultra-high molecular weight fibers. While these materials are effective to provide the desired structural strength to the stent, they suffer from the drawback that they have very long degradation time. This can lead to issues such as foreign body reactions.

It is also difficult to vary the composition of the stent over its length in order to provide variable strength and/or flexibility in different regions of a stent. For example, in order to make a region more flexible normally requires making the stent thinner, while increasing strength typically requires the stent framework to be thicker. As a result, strength and flexibility are generally opposing outcomes of stent design.

An additional advantage provided by stents is that they allow for treatment of medical conditions using minimally invasive transcatheter delivery methods. To make use of minimally invasive transcatheter delivery methods typically requires that the stent material be visualizable using medical imaging techniques such as fluoroscopy. In order to do this, the stent must include a radio-opaque material that can be visually distinguished from surrounding anatomical structures.

Like is done with therapeutic agents incorporated into stents, frequently the radio-opaque material is co-extruded with the polymeric fiber. However, this technique alters the mechanical properties of the stent, as well as reduces the proportion of the stent that is available for inclusion of the desired therapeutic agent(s).

Thus, there is a need not met by the prior art for a polymeric stent that is generally bioabsorbable, which can be variably flexible over the length of the stent, which provides openings to branching vessels, and which can be visualized by conventional medical imaging techniques both during and after placement into a patient.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints and open-ended ranges should be interpreted to include commercially practical values. Similarly, all lists of values should be considered as inclusive of intermediate values unless the context indicates the contrary.

SUMMARY OF THE INVENTION

The inventive subject matter provides an expandable stent that provides features and improvements over prior art stents. In one aspect, the stent is formed from one or more substantially contiguous primary fibers that, in the furled state, form a coiled-coil structure. The fibers generally describe a helical pattern around a major longitudinal axis of the stent. The primary fibers include, at various intervals, secondarily coiled regions. In some embodiments, in the expanded state, these secondary coils are arranged around one or more lateral axes that run substantially parallel to the major axis of the stent.

The stent also provides for variable spacing in the pitch spacing of the primary fiber. In some embodiments, pitch is varied in sub-regions of the stent in order to provide for local variation in stent flexibility and rigidity without having to alter the composition or dimensions of the primary fibers.

The stent may include longitudinal support rods that run substantially the length of the deployed stent. In addition, the stent may also include longitudinal regional support rods that run less than the full length of the deployed stent. By providing short support rods as compared to prior art stents, defined points of increased flexibility can be provided without substantially compromising the overall strength of the stent. Breaks between rods also allow for variable regions of primary fiber curvature radius in order to provide regions of the stent that can be extended from a main vessel into a branch vessel, or into the neck of an aneurysm to aid in promoting resolution and hemostasis.

The stent further includes radio-opaque micro-tubes that are designed to be visible using conventional medical imaging methods. These micro-tubes can be placed at desired locations on the primary fibers and/or support fibers in order to mark specific locations on the stent.

Various objects, features, aspects and advantages of the inventive subject matter will become more apparent from the following detailed description of preferred embodiments, along with the accompanying drawing figures in which like numerals represent like components.

DETAILED DESCRIPTION

The present invention is based on the need to provide a bioabsorbable stent that has both high strength and flexibility. The stent also provides additional features and advantages such as variably flexible regions, radio-opacity and drug-elution ability. The stent also provides for being convertible between a furled state and expanded state. The stent in a furled state is mounted on a balloon catheter that is easily delivered to a desired location in vivo. When at the desired location, the stent can be readily unfurled to the expanded state, which provides the intended structure for therapeutic effectiveness.

Figure 1:
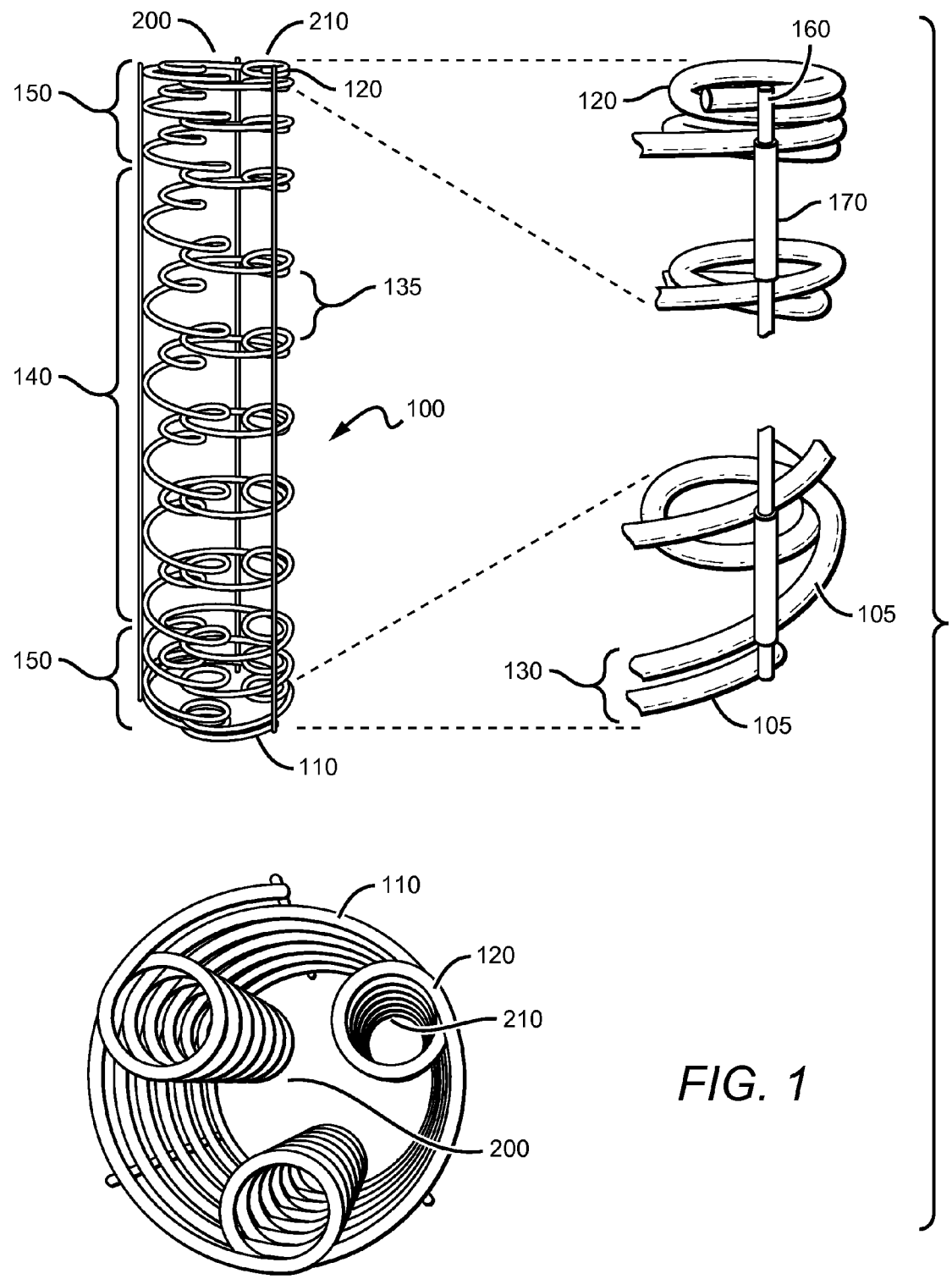
FIG. 1 is a schematic illustration of the three-dimensional structure of an expandable coil stent according to an embodiment of the present invention. The top panel shows a side view of an embodiment of the stent, while the bottom panel shows an end-on view.

As can be seen in FIG. 1, the stent 100 generally comprises a coiled-coil structure formed by differentially curving a substantially continuous primary fiber or fibers 105 along the fiber length. Primary coils having the larger radius 110 are oriented around a major longitudinal axis 200, while secondary coils 120 are oriented around one or more lateral longitudinal axes 210. Each lateral axis is substantially parallel to the major axis and to each other. In the embodiment depicted in FIG. 1, the stent material is formed into a coiled-coil structure having a major longitudinal axis, and three lateral axes spaced approximately equally around the major axis. It may be desirable to provide a stent having numbers of lateral axes other than 3, and so the invention is not intended to be limited to stents having only three lateral axes.

In some cases the stent can comprise a single fiber formed into the coiled-coil structure, while in other embodiments, the stent can comprise two or more co-linearly arranged fibers following a common path 130. Even more fibers can be included in a stent depending on the degree of strength that is desired. The presence of co-paired fibers also lends itself to the manufacture of bifurcation stents, such as those described in U.S. patent application Ser. No. 13/476,336, which is co-owned by the inventor.

As can be appreciated from the figures, secondary coils are formed by decreasing the radius of curvature within sections along the length of the primary fiber or fibers. The periodicity of secondary coils can in some cases be designed to occur at substantially the same points around the major circumference of the stent 100 as exemplified in FIG. 1. When formed in this way, secondary coils will generally align around a lateral axis that is substantially parallel to the major longitudinal axis of the stent. For example, where secondary coils are formed at a distance of ⅓ of the stent circumference apart from each other, the result will be secondary coils aligned relative to three lateral axes running substantially parallel to the major longitudinal axis of the stent.

In other cases, secondary coils may be disposed at intervals more or less than an integer fraction of the stent circumference, in which case the lateral axes formed by secondary coils will follow a helical path winding around the major longitudinal axis. Stiller further, the relative size of the furled and expanded states can be varied by varying the spacing of the secondary coils. For example, where the secondary coils are placed relatively close together, the final expanded circumference of the stent will generally be larger than if secondary coils are spaced farther apart.

As discussed above, one of the problems inherent in stent design is providing a stent with sufficient strength and which is also flexible. This is especially important in smaller and tortuous vessels and ducts since weakened structure may be prone to additional damage caused by the stent exerting a force against the walls of the vessel or duct where it is placed.

For the reason, the present invention provides for regions of variable pitch of the coiled-coil structure. As shown in FIG. 1, it is possible to form a stent having differing pitch spacing 135 between adjacent coils. For example, FIG. 1 depicts and embodiment of stent where the pitch spacing of coils is wider in the central portion 140 of the stent, and closer spaced at the ends 150. Decreasing the pitch spacing 135 of coils results in increased regional strength of the stent, without having to alter the composition of the fiber from which it is formed. Various combinations of pitch spacing are compatible with the design of the present stent. For example, it some cases it may be desirable to make the stent more rigid in the central portion, wherein the pitch spacing would be relatively smaller compared to the ends. It might also be desirable to have one end relatively more rigid than the opposite end, and this is contemplated as well in the current design as described herein.

Figure 2:
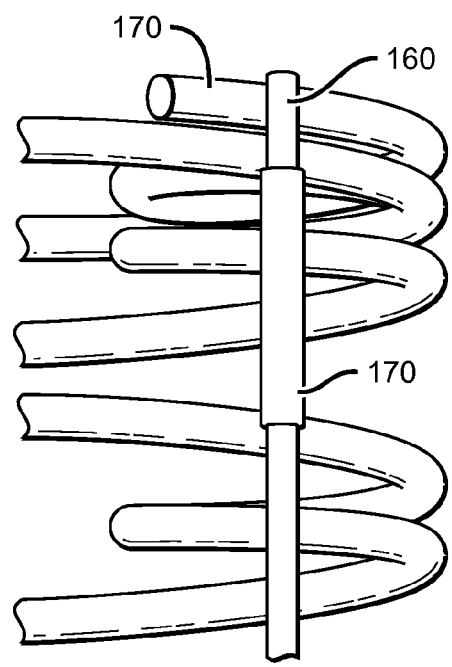
FIG. 2 is a perspective view of an embodiment of a stent depicting radio-opaque micro-tubes.
Figure 3:
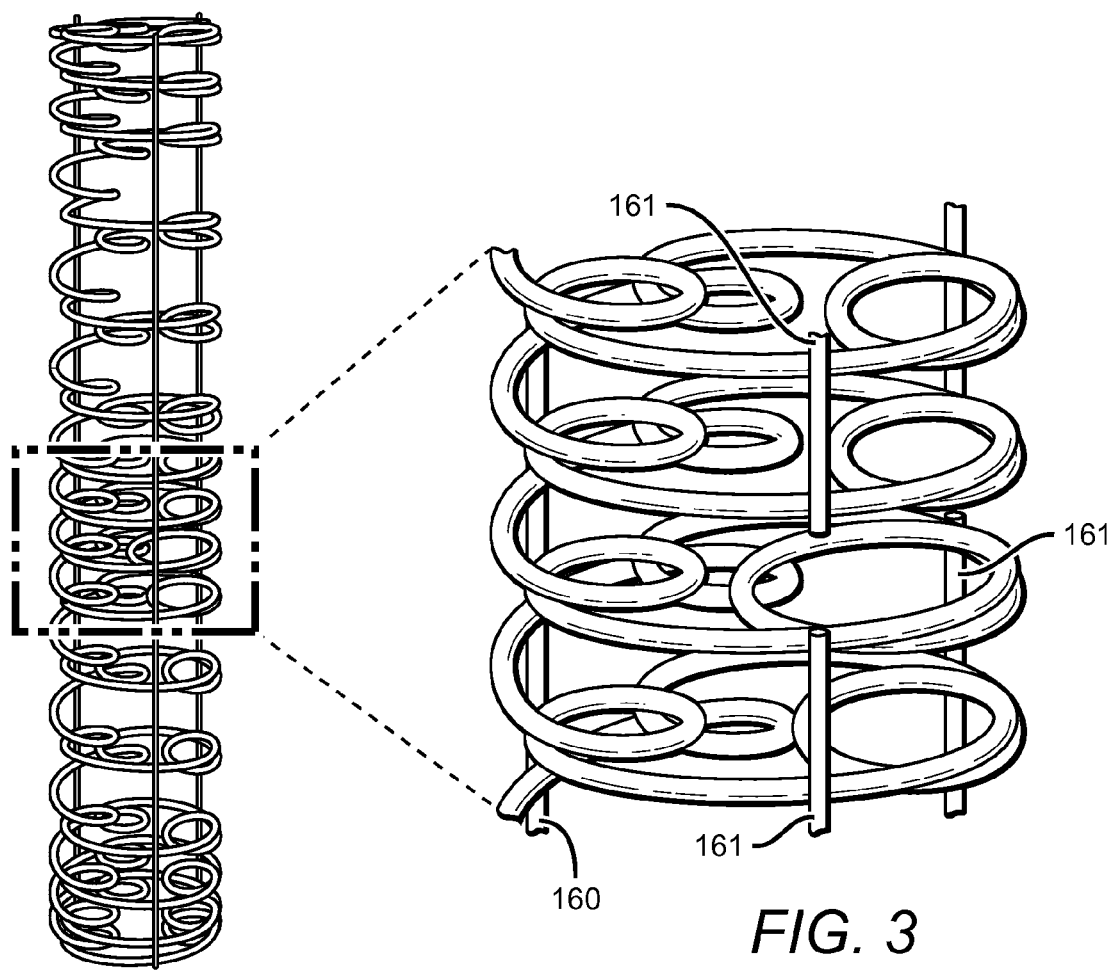
FIG. 3 is a side view of an embodiment of a stent, depicting further detail of exemplary secondary coils and discontinuous longitudinal support fibers.

Strength and flexibility of the stent can also be varied by the inclusion of longitudinal support fibers 160 disposed along the outer aspect of the stent. As shown in FIGS. 1-3, support fibers 160 are located generally parallel to the major axis of the stent, and extend over substantially the length of the deployed stent. Support fibers serve two primary functions when present in the stent. First, they can be used to vary the flexibility and strength of the strength, without changing the general composition or size of the primary fibers. As discussed above, one way to make stents stronger is to increase fiber diameter. However, this increases the time required for bio-absorption, which may in turn lead to complications such as chronic foreign body responses. Using support fibers to improve strength avoids this problem. Similarly, support fibers can be used to maintain the pitch spacing of coils within the stent.

Figure 4:
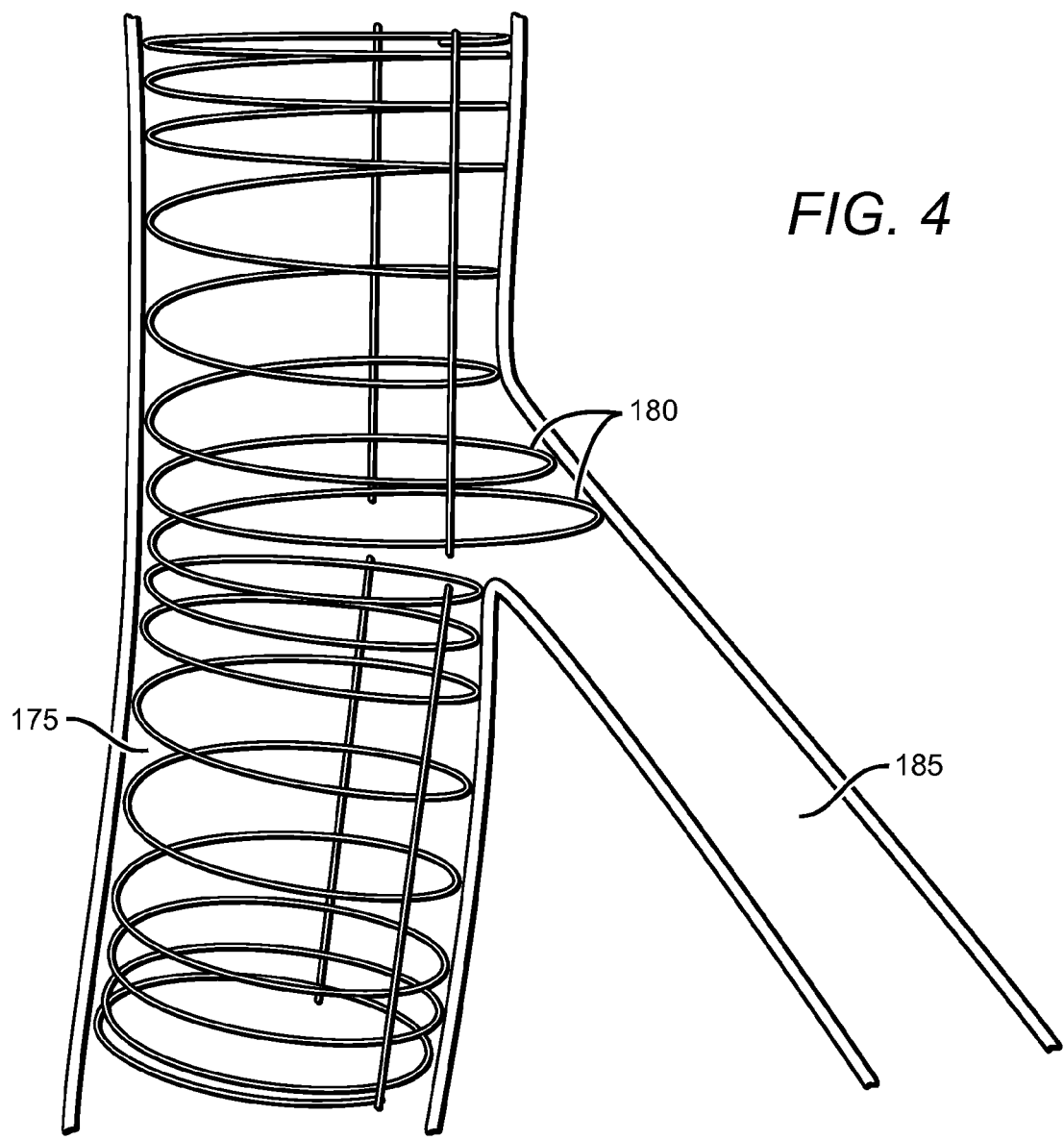
FIG. 4 is a schematic representation of an embodiment of a stent deployed at a junction between a main vessel and a branch vessel.

In contrast to prior art stents that include support fibers running the length of the stent, the present invention, as shown in in FIG. 3, also includes regional support fibers 161 that extend along a portion of the length of the deployed stent. As such, there are provided gaps along the length of the stent between successive regional support fibers 161. This provides a further advantage in creating a localized zone of increased flexibility along the stent, as shown in FIG. 3. Breaks in the regional support fibers also allow for localized regions where the curvature of the primary fiber can be increased in order to locally increase the apparent diameter of the stent. As shown in FIG. 4, in conjunction use with a kissing balloon catheter (not shown), this provides for an out bowing 180 of a portion of the stent, which can be useful when the stent is deployed in a main vessel 175 at a branch point with a second vessel 185.

Conveniently, a stent like the example provided in FIG. 4, may also be useful in stabilizing and promoting healing of aneurysms. As is well known, aneurysms form at regions of local weakening in an arterial wall. They are generally classified as being saccular or fusiform. Saccular aneurysms are generally spherical in shape and involve only a portion of the arterial wall, and have a lumen that is usually partially or completely filled by a thrombus. In contrast, fusiform aneurysms are variable in both length and diameter, extending up to 20 cm. As the size of an aneurysm increases, so does the risk of rupture with resulting hemorrhage and potentially death of the patient.

Where the wall has weakened to the extent that the artery balloons outwards, the out pocketing of the arterial wall is not unlike a branching vessel. As a result, the stent provides a tool with which to potentially stabilize and promote the healing and hemostasis of aneurysms. A stent such as has been described can be fabricated to provide a variable pitch region that extends into the neck and potentially into the sac of an aneurysm. Stent fibers located within the neck and/or sac region will potentially result in localized micro-eddies in the local blood flow. This turbulent flow will promote hemostasis, thus limiting further blood flow into the aneurysm. Over time the aneurysm sac will shrink, the thrombus will resolve, and the risk of rupture will be significantly reduced. In some cases it will be desirable to provide a stent that includes pharmaceutically effective compounds that are able to reduce inflammatory responses in the arterial wall in the vicinity of the aneurysm neck, to promote localized clotting in order to limit further expansion of the sac, or to generally promote tissue repair.

It is also possible to vary the number, spacing, thickness or length of individual support fibers depending on the region of the stent. For example, in some cases, where greater rigidity is required, fibers more closely spaced may increase rigidity. Similarly, support fibers with increased diameter will be generally more rigid than ones with a smaller diameter.

The stent can further include micro-tubes 170 that are radio-opaque. As shown in FIGS. 1 and 2, these micro-tubes can be incorporated with the primary fibers or the support fibers or both. Micro-tubes can be placed in order to mark one or both ends of the stent. They can also be disposed at locations along the length of the stent in order to mark certain positions. For example, in some embodiments, micro-tubes may be used to mark breaks between support fibers in order to identify relatively more flexible regions of the stent. Similarly, micro-tubes could be placed to identify the location of regions of the stent designed to be able to bow out and be positioned at the junction of a main vessel and branch vessel. Using a micro-tube allows one to manufacture a stent with markers visible by medical imaging techniques without having to comprise the entire structure of the stent.

Both primary fibers and support fibers may also be designed in a number of configurations. For example, primary fibers and support fibers may be solid, multi-layered or hollow. Primary and support fibers are generally constructed of bioabsorbable polymeric material. Example of suitable materials include, but are not limited to polydioxanone, polyglycolide, polycaprolactone, polylactides, poly-L-lactide, poly-D,L-lactide, poly (L-lactide-co-glycolide), poly (D,L-lactide-co-glycolide), poly (Llactide-co-D,L-lactide), poly (L-lactide-co-trimethylene carbonate), polyhydroxyvalerate, or ethylvinylacetate. Mixtures of two or more of the above-listed polymers can also be used to manufacture the stent.

The specific polymer(s) used to make the fibers can be selected depending on the desired degradation time required for a particular application. Degradation will be affected by the specific chemical composition of the fiber, the molecular weight of the polymer, and the diameter of the fiber that is formed, along with other materials such as therapeutic agents. It will be apparent to those of skill in the art as to the desired composition of a fiber for any particular application.

The stent can also be a drug-eluting stent, the term "drug" generally referring to any therapeutically effective compound. For example, compounds that inhibit restenosis, promote healing, promote wound healing or reduce inflammatory response, or inhibit foreign body responses can be included in the fiber, either as part of the fiber itself, in layers disposed on the fiber, or within a lumen formed in a hollow fiber. When included as part of the stent fiber, the drug can comprise from 0.1 to 99.9% of the material used to form the stent fiber(s).

The present invention also provides a method of treating a body passageway in need of treatment. As defined herein, the term body passageway generally refers to blood vessels, ducts, and similar anatomical structures that include a lumen. Stents are typically used to support these types of structures, for example where the lumen has narrowed such as occurs in atherosclerosis. Using stents such as described, it is possible to take a stent in the furled configuration, and then using minimally invasive methods such as percutaneous catheters, to position the stent at a location in the lumen of a passage that is in need of treatment. Once positioned, the stent can then be converted from the furled to the expanded state, thereby re-opening and supporting the passageway (i.e., vessel, duct or like structure).

In some cases, the "lumen" may comprise the neck of an aneurysm or the branch point of a vessel. In these cases, a region of variable pitch may be provided in the stent, such that in the expanded state, a portion of the stent extends into the neck of the aneurysm or the branch. In this way, the stent can further support these particular regions, as well as the lumen of the main vessel or other passage into which the stent has been placed. In the case of an aneurysm, the stent may further be fabricated to include compounds effective to promote hemostasis, reduce inflammation, or to promote general healing of the aneurysm and surrounding portions of the vessel. As described above, the method of placing a stent that is expandable and which has the ability to extend to an partially conform to the lumen of an aneurysm may assist in promoting hemostasis by producing turbulent flow that may promote clotting.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An expandable stent comprising:
a single filament shaped into a primary coil having a plurality of primary coil segments that each include a plurality of elements, the stent having a first diameter when the stent is in a furled configuration;
a plurality of longitudinal support fibers coupled to the filament, wherein at least one longitudinal support fiber is disposed along an outer aspect of the stent and is parallel to a major axis of the stent and extends along the entire length of the stent;
wherein at least one of the elements is expandable beyond others of the elements and arranged such that upon expansion of the elements the stent assumes an unfurled configuration having two distinct diameters at two distinct primary coil segments, and wherein the first diameter is smaller than the two distinct diameters; and
wherein at least another one of the longitudinal support fibers is discontinuous at a location between the two distinct primary coil segments to allow formation of a localized zone of increased radius or curvature along a longitudinal axis of the stent.

2. The expandable stent of claim 1 wherein the plurality of elements are configured as a plurality of secondary coils.

3. The expandable stent of claim 1 wherein each of the primary coil segments comprises at least three elements.

4. The expandable stent of claim 1 wherein at least one element in a first primary coil segment is vertically aligned with at least one element in a second primary coil segment.

5. The expandable stent of claim 1 wherein a further one of the plurality of longitudinal support fibers is continuous at the location between the two distinct primary coil segments.

6. An expandable stent comprising:
a single filament shaped into a primary coil having a plurality of primary coil segments that each include a plurality of elements having a decreased radius of curvature in a furled configuration compared to a radius of curvature of the elements in an unfurled configuration;
wherein the filament comprises a bioabsorbable polymer;
a first longitudinal support fiber disposed along an outer aspect of the stent and is parallel to a major axis of the stent and extends across at least two primary coil segments to thereby increase stability of the stent, and wherein the first longitudinal support fiber extends along the entire length of the stent;
a first regional support fiber extending only along a portion of the length of the stent and configured to allow formation of a localized zone of increased radius or curvature along a longitudinal axis of the stent.

7. The expandable stent of claim 6 further comprising a second regional support fiber, and wherein the first regional support fiber and the second regional support fiber are lying along a common axis and longitudinally spaced from one another.

8. The expandable stent of claim 7 wherein a first primary coil segment has a radius of curvature that is different from a second primary coil segment, and wherein a transition from the first to the second primary coil segment is located at a location between the first and second regional support fibers.

9. The expandable stent of claim 6 wherein a first primary coil segment has a radius of curvature that is different from a second primary coil segment.

10. An expandable stent comprising:
a single filament shaped into a primary coil having a plurality of primary coil segments and first and second sets of secondary coil segments, wherein the first and second sets of secondary coil segments are disposed within each of the primary coil segments;
wherein the filament comprises a bioabsorbable polymer;
a plurality of longitudinal support fibers coupled to the filament, wherein at least one longitudinal support fiber is disposed along an outer aspect of the stent and is parallel to a major axis of the stent and extends across at least two primary coil segments;
wherein the stent has a first stent diameter when the stent is in a furled configuration;
wherein at least one secondary coil segment of the first set of secondary coil segments has a first coil diameter, and wherein the second set of secondary coil segments has a second coil diameter, wherein the first coil diameter is larger than the second coil diameter;
wherein the first and second sets of secondary coil segments are configured such that, when the stent in an unfurled configuration, the stent has a second stent diameter and a third stent diameter, wherein the second and third stent diameters are larger than the first stent diameter, and wherein the second stent diameter is larger than the third stent diameter; and
wherein at least one of the longitudinal support fibers is configured to allow localized flexing of the stent about a longitudinal axis of another of the longitudinal support fibers.

11. The expandable stent of claim 10 wherein a first set of the plurality of primary coil segments have a first helical pitch angle, wherein a second set of the plurality of primary coil segments have a second helical pitch angle, and wherein first and second helical pitch angles are different.

12. The expandable stent of claim 10 wherein the at least one of the longitudinal support fibers is discontinuous at a location of the second stent diameter.

13. The expandable stent of claim 10 wherein the stent is configured such that the second stent diameter is located where the first set of secondary coil segments is unfurled.

14. The expandable stent of claim 10 further comprising a radio-opaque label.

15. The expandable stent of claim 10 wherein the first set of the secondary coil segments are vertically aligned relative to each other.

* * * * *